United States Patent [19]

Browne et al.

[11] Patent Number: 5,632,275
[45] Date of Patent: May 27, 1997

[54] CATHETER LAB TABLE PAD AND METHOD FOR USING THE SAME

[75] Inventors: Kevin F. Browne, Lakeland, Fla.; Robert M. Scribner, Boulder, Colo.

[73] Assignee: Scribner-Browne Medical Design Incorporated, Boulder, Colo.

[21] Appl. No.: 308,099

[22] Filed: Sep. 16, 1994

[51] Int. Cl.$^6$ ....................................................... A61B 5/05
[52] U.S. Cl. ...................... 128/653.1; 378/208; 378/209; 5/601
[58] Field of Search ........................... 128/653.1; 5/453, 5/455, 456, 461, 600, 601, 612, 615, 632, 644, 645; 378/204, 208, 209; 600/195

[56] References Cited

U.S. PATENT DOCUMENTS

| | | | |
|---|---|---|---|
| 4,914,771 | 4/1990 | Afeyan | 5/456 |
| 4,926,457 | 5/1990 | Poehner et al. | 378/208 |
| 5,044,029 | 9/1991 | Vrzalik | 5/453 |
| 5,067,189 | 11/1991 | Weedling et al. | 5/81 |
| 5,070,559 | 12/1991 | Petifer | 5/455 |
| 5,083,550 | 1/1992 | Kraus et al. | 128/653.1 |
| 5,090,076 | 2/1992 | Guldager | 5/453 |
| 5,121,512 | 6/1992 | Kaufmann | 5/455 |
| 5,129,911 | 7/1992 | Siczek et al. | 128/653.1 |
| 5,168,589 | 12/1992 | Stroh et al. | 5/455 |
| 5,189,742 | 3/1993 | Schild | 5/453 |
| 5,243,721 | 9/1993 | Teasdale | 5/453 |
| 5,243,723 | 9/1993 | Cotner et al. | 5/455 |
| 5,265,610 | 11/1993 | Darrow et al. | 128/653.1 |
| 5,267,364 | 12/1993 | Volk | 5/453 |
| 5,287,577 | 2/1994 | Bremer et al. | 5/601 |

*Primary Examiner*—Marvin M. Lateef
*Assistant Examiner*—Brian L. Casler
*Attorney, Agent, or Firm*—Sheridan Ross P.C.

[57] ABSTRACT

A catheter lab imaging apparatus for imaging a heart region of a patient positioned thereon. The apparatus includes a catheter lab table, an x-ray imager positioned about the table and including a transmitter and a receiver, the transmitter being pivotable relative to the table to image the patient along predetermined imaging axes, a catheter lab table pad for supporting the patient on the table. The pad includes a top radiolucent layer defining a top surface of the pad and bottom radiolucent layer defining a bottom surface of the pad, the bottom layer being joined to the top layer around the periphery thereof to define at least one sealed chamber for supporting the patient. The pad may further include at least one interior seam positioned within the chamber to limit separation between the top layer and the bottom layer, wherein each of the interior seams is positioned such that each of the predetermined imaging axes avoids intersection with all of the interior seams when a patient is positioned on the pad.

12 Claims, 8 Drawing Sheets

CATHETER LAB TABLE PAD AND METHOD FOR USING THE SAME

FIELD OF THE INVENTION

The present invention generally relates to medical lab table pads and, more specifically, to an inflatable catheter lab table pad which is designed to comfortably support a patient on a table during catheter lab imaging procedures.

BACKGROUND OF THE INVENTION

Table pads are typically used in the medical industry to provide support and/or comfort to a patient lying on a medical table. For example, pads are sometimes positioned on a standard hospital bed to provide further comfort to the patient. Furthermore, pads have been used to support a patient during surgical procedures.

Pad designs have taken on many forms to meet specific needs. For example, soft urethane foam pads (e.g., about ¼ inch thick) have been utilized to provide comfort to patients while lying on a hard surface such as a surgical table. Such foam pads are relatively inexpensive and can be readily washed or thrown away after the medical procedure has been performed. In addition, inflatable medical pads have been designed to reduce pressure sores associated with long-term patient immobility. Such inflatable pads may comprise an air permeable but waterproof fabric which provides an airflow around the patient. Such airflow reduces skin breakdown by reducing the contact between skin and moisture, the moisture being withdrawn by the airflow.

Although the above-noted medical pads have met with some commercial success, these products tend to not provide sufficient patient comfort and/or tend to be relatively expensive to manufacture. For example, although relatively inexpensive, urethane foam does not adequately compensate for the contour of the human body, and further does not adjust for different patient weights. The air permeable pads tend to be relatively expensive to manufacture and can be expensive to operate since they require a constant source of pressurized air to maintain the pad at proper inflation.

When utilized to support a patient on an imaging apparatus (e.g., an x-ray imager), medical pads must be substantially radiolucent to avoid the formation of image artifacts. Such image artifacts can be caused by medical pads which have varying thicknesses in the region where imaging is being performed. For example, the placement of a pad seam directly in line with an imaging axis will likely result in the formation of an image artifact, which may interfere with the performance of the imaging operation. This is likely one reason why inflatable pads are not currently favored for use in imaging applications.

Radiolucency is also important to reduce the amount of radiation required to form a suitable image. More specifically, if a table pad is not substantially radiolucent, the imaging apparatus will typically automatically compensate by increasing the level of radiation being transmitted by the apparatus. This increase in radiation can be harmful to medical personnel. In addition, scatter of the radiation (i.e., as opposed to absorption) caused by non-radiolucency can undesirably come into contact with medical personnel. The quality of the x-ray image may be compromised as the pad absorbs a portion of the transmitted radiation.

During catheter lab procedures, where the heart is typically imaged, it is most-important for the pad to be radiolucent in the upper torso region. In addition, for such procedures, fluids that are generated during the catheter procedure (e.g., blood, contrast media, body fluids, etc.) should be prevented from migrating toward the upper torso section to avoid such fluids interfering with the imaging.

Accordingly, it is an object of the present invention to provide a catheter lab pad which is radiolucent in an area of interest (e.g., in the upper torso section of the pad to accommodate catheter lab imaging of the heart). It is a further object of the present invention to design an inflatable catheter lab pad wherein longitudinal seams are precisely positioned to avoid interference with imaging axes. Such pad will further be designed to accommodate the presence of fluids generated during catheter lab procedures so that such fluids do not interfere with the imaging.

SUMMARY OF THE INVENTION

In accordance with the present invention, a catheter lab pad is provided which accomplishes one or more of the above-stated objectives. The pad is designed to be used on a catheter lab imaging apparatus for imaging a heart region of a patient positioned thereon. Such catheter lab apparatuses typically comprise a catheter lab table and an x-ray imager, including a transmitter and a receiver, positioned about the table. The transmitter is pivotable relative to the table to image the patient along predetermined imaging axes (e.g., at 0°, 30°, 45° and 60° relative to an axis perpendicular to the table top surface).

The pad of the present invention is positionable on the table and includes a top radiolucent layer defining a top surface of the pad and a bottom radiolucent layer defining a bottom surface of the pad. The bottom layer is joined to the top layer around the periphery thereof to define at least one sealed chamber for supporting the patient. The top and bottom layers may comprise separate pieces of material or, alternatively, may comprise a single piece of material configured to form a chamber. The pad further comprises at least one interior seam positioned within the chamber to limit separation between the top and bottom layers, wherein each of the interior seams is positioned such that each of the predetermined imaging axes avoids intersection with all of the interior seams when a patient is positioned on the pad.

In one embodiment, the pad includes at least two interior seams positioned about 6.5 inches apart from each other and equally disposed on opposing sides of a central longitudinal axis of the pad. A central region of the pad between the two interior seams is substantially free of interior seams, thereby providing a "seam-free" region for imaging the heart of the patient (e.g., when the apparatus is imaging at the 0° position). Such distance between the two interior-most seams may vary depending on particular variables, such as imaging angles, patient size, patient weight, pad thickness, etc., the general concept being to provide interior seams which do not interfere with imaging axes and which are sufficiently spaced to allow seam-free imaging.

To prevent air from leaking from the pad, and to correspondingly avoid the need to constantly supply pressurized air to the pad, the top and bottom layers of the pad preferably each comprise a substantially air impermeable coating. In one embodiment, such coating comprises urethane (e.g., about 0.003 inches thick). Preferably, such substantially air impermeable coating is positioned on both sides of each of the top and bottom layers.

As noted, in order for the pad to be usable in a catheter lab procedure, the pad must be radiolucent, at least in the region where the patient's heart will be positioned. In this regard, the top and bottom layers of the pad each are comprised of radiolucent material, such as woven nylon (e.g., having a fineness of at most about 70 denier).

When utilizing the pneumatic pad during catheter lab imaging on the heart of a patient, the process generally comprises the steps of positioning a pneumatic pad on the table with a radiolucent portion of the pad positioned in an imaging region of the table, inserting gas into the pad to at least partially inflate the pad, positioning the patient in a reclined position on the pad such that the patient's heart is aligned with the radiolucent portion of the pad, imaging the heart of the patient while performing a catheter lab procedure, removing the patient from the pad, and removing gas from the pad to deflate the pad. The process does not necessarily require the steps to be performed in the above-recited order, as will become apparent from the discussion herein.

In one embodiment, the pad is initially positioned on the table with a radiolucent portion of the pad positioned in an imaging region of the table. Next, gas is inserted into the pad to at least partially inflate the pad and the patient is positioned thereon in a reclined position such that the patient's heart is aligned with the radiolucent portion of the pad. The patient's heart is then imaged while performing a catheter lab procedure (e.g., angiography, atherectomy, angioplasty, etc.). Finally, the patient is removed from the pad and gas is removed from the pad to deflate the pad.

The pad utilized in the process of the present invention may comprise seams, and the imaging apparatus may image along predetermined imaging axes (e.g., 0°, 30°, 45°, and 60° relative to an axis extending perpendicular to the table). In such a situation, it may be beneficial to modify the process such that the pad positioning step comprises positioning the seams to avoid interference with the imaging axes. As noted above in the description of the pad and apparatus, such a positioning of the pad seams relative to the imaging axes may reduce or eliminate image artifacts associated with the seams.

In one embodiment, the inflating step occurs before the patient positioning step. In such an embodiment, the inflating step may comprise filling the pad with gas to a pressure of less than about 1 psi, and preferably a pressure of about atmospheric pressure. For example, the inflating step may comprise filling the pad with gas to less than maximum volume of the pad. Such an inflating step would provide segments of the pad which are not completely filled, thereby giving the segments a generally non-circular cross-section, which advantageously reduces the likelihood that the material adjacent the seams will be perpendicular to the seams and parallel to the incoming radiation. In addition, incomplete inflation provides a more comfortable surface for the patient since the patient will have more surface area contact with the pad, thereby reducing pressure points.

In another embodiment, the patient is positioned on the pad prior to inflation of the pad. In this process, the pad must be inflated to greater than atmospheric pressure (i.e., to lift the patient off of the table), but is preferably inflated to less than or equal to about 2 psi to enhance patient comfort. When the pad includes at least head and torso sections, the patient may be placed on the pad before the torso section is inflated and after the head section is inflated, thereby providing a pad for the patient's head immediately when the patient reclines.

A waterproof cover (e.g., polyethylene sheet) may be utilized in conjunction with the pad to avoid soiling the pad. In this regard, the process may further include the steps of positioning a waterproof cover on the pad before the patient is positioned on the pad. Likewise, the process may further include the step of removing the waterproof cover from the pad after patient is removed from the pad. Preferably, the cover includes means for detachably securing the cover to the pad (e.g., adhesive, preferably double sided adhesive tape) to cover at least a portion of the top surface of the pad. More preferably, the cover wraps around the peripheral intersection between the top and bottom layers and is secured to the bottom layer by the means for detachably securing.

In one embodiment, the waterproof cover is bag-shaped to substantially cover top, bottom and at least one end of the pad. Correspondingly, after the waterproof cover is removed, the waterproof cover may be turned inside out and used to contain waste produced during the imaging step.

The cover may include an absorbent material secured (e.g., detachably) thereto for absorbing fluids. When absorbent material is used, the process may further comprise the step of positioning the absorbent material under the upper leg and hip region of the patient. Such absorbent material absorbs fluids (e.g., contrast media, body fluids, etc.) which may be generated during performance of the imaging procedure, and substantially prevents such fluids from travelling away from the upper leg and hip region of the patient and potentially interfering with the imaging process. After the imaging procedure, the process preferably further comprises the step of detaching the absorbent material from the cover.

In another aspect of the present invention, an inflatable pad for use in supporting a patient is provided. The pad generally comprises a top layer defining a top surface of the pad and a bottom layer defining a bottom surface of the pad. The bottom layer is joined to the top layer around the periphery thereof to define at least one chamber for containing fluid to support the patient. The pad is further provided with a valve means for automatically relieving fluid from the chamber (e.g., a relief valve) when the pressure within the chamber exceeds a predetermined value (e.g., about 2 psi). Such valve means prevents over-inflation of the pad, and further allows for automatic deflation of the pad during performance of cardiopulmonary resuscitation. Preferably, such valve means is positioned on the bottom layer and protrudes from the pad at an angle of between about 10° and about 80°, and preferably between about 30° and about 60°, below a plane defined by the top surface of the pad.

DETAILED DESCRIPTION

FIGS. 1–7 illustrate a pneumatic table pad 11 embodying the features of the present invention. Although the present invention will be described with reference to support of a patient on an x-ray imaging table, it should be appreciated that the present invention is also applicable to other applications where a patient is supported on a surface. For example, the present invention could be used in other internal imaging applications, such as radiological imaging or magnetic resonance imaging (MRI).

Figure 1:
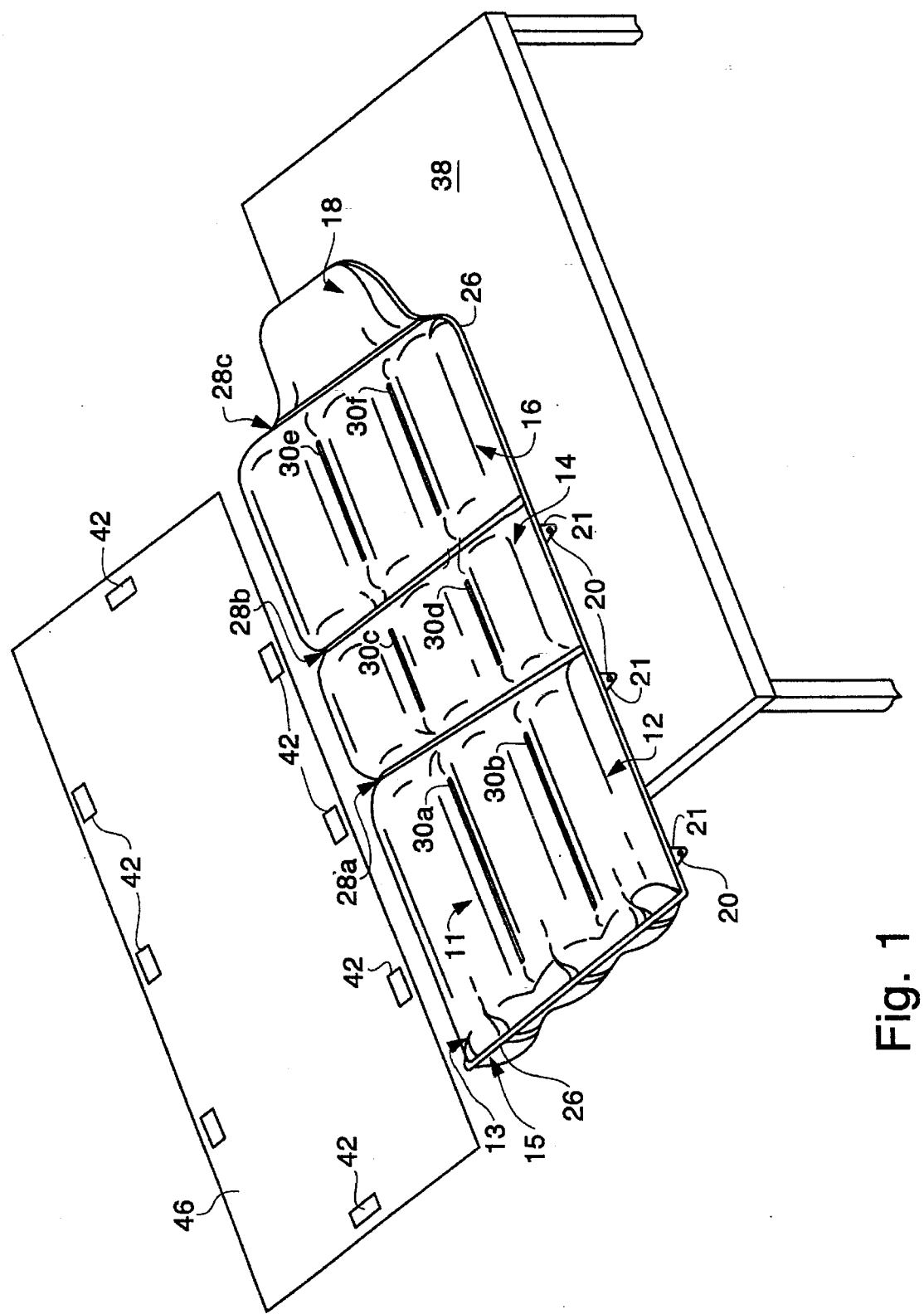
FIG. 1 is an exploded perspective view of an inflated table pad and cover embodying the present invention.
Figure 2:
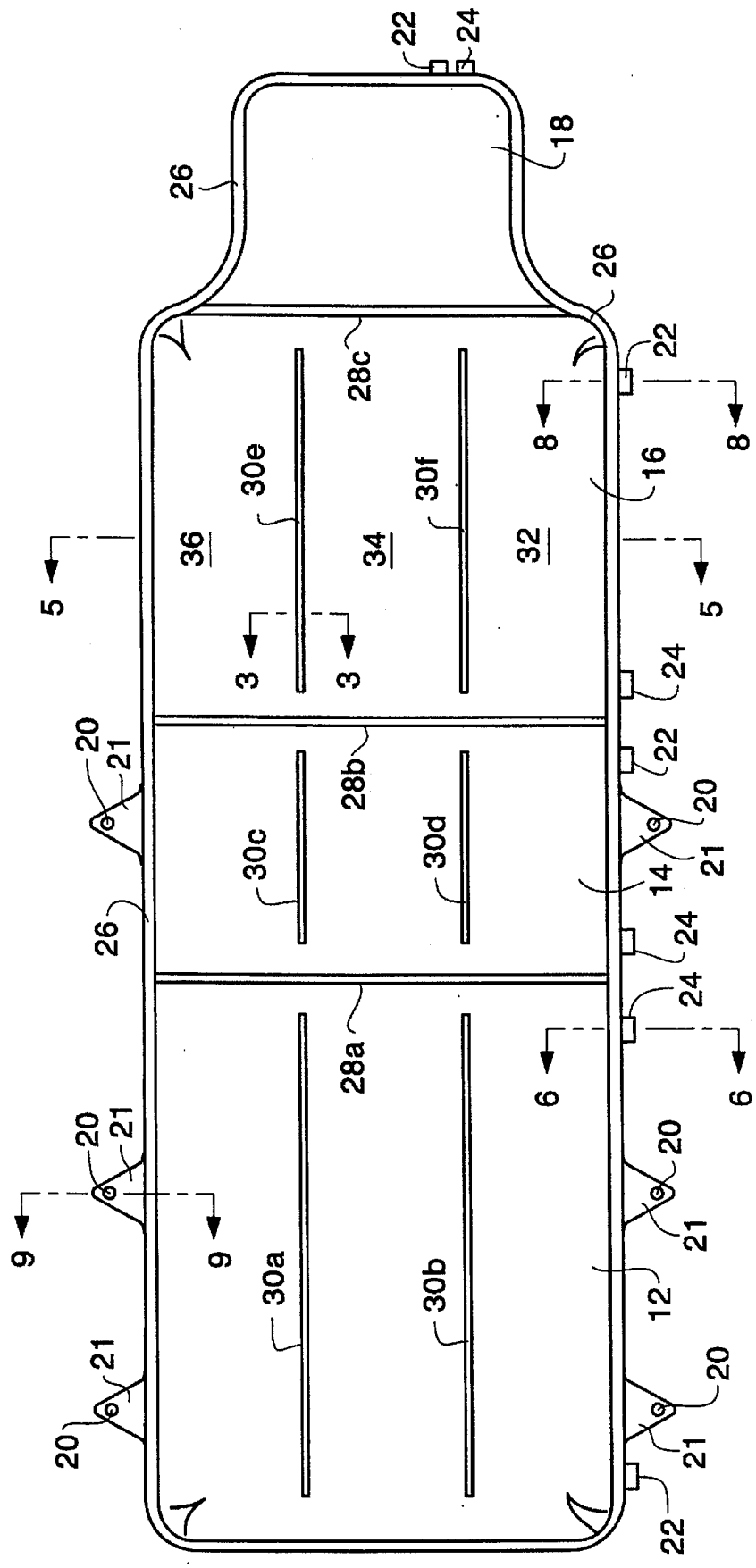
FIG. 2 is a top view of the table pad of FIG. 1 in a deflated condition.
Figure 3:
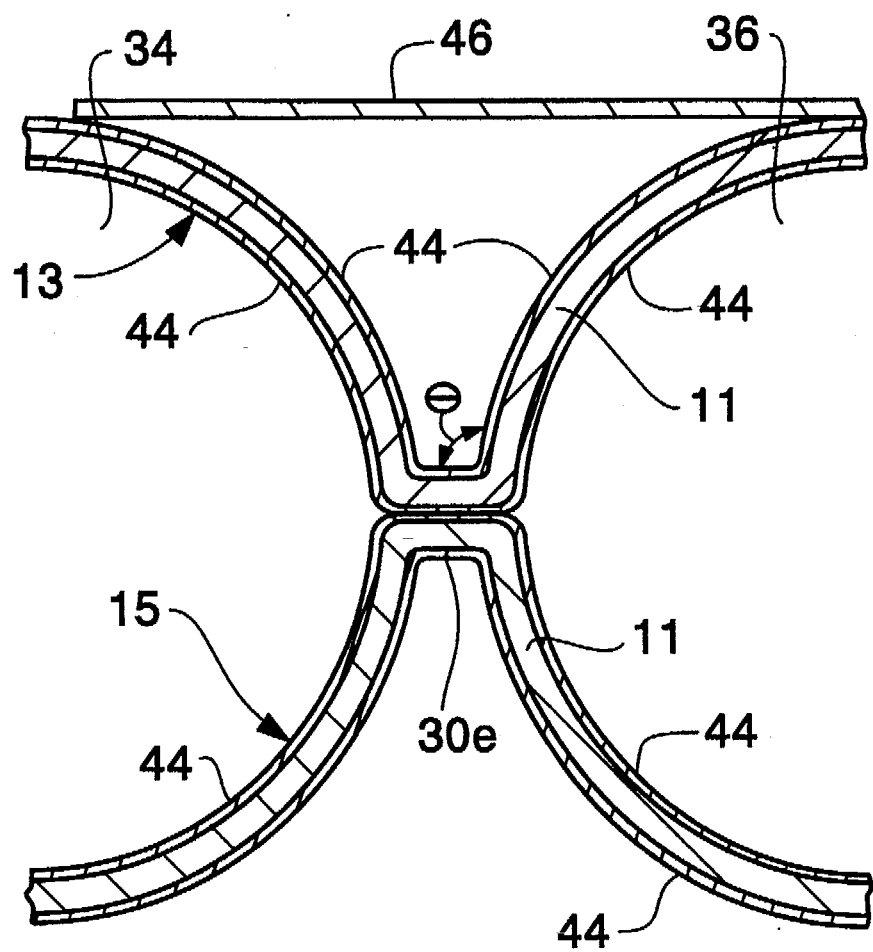
FIG. 3 is an enlarged section view of a longitudinal seam and adjacent material of the table pad, taken along line 3—3 in FIG. 2.

Referring to FIGS. 1–3, the illustrated pad 11 generally comprises two sheets of material 13, 15 appropriately secured to each other to form separately inflatable chambers. More specifically, the two sheets of material 13, 15 are joined together around the perimeter thereof to form a perimeter seam 26 completely around the outer edges of the pad. Alternatively, the pad 11 may comprise one sheet of material folded along a longitudinal axis and joined together around the perimeter thereof to form a perimeter seam 26 around the outer edges of the pad. In addition, lateral seams 28a–c are formed to define a leg chamber 12, a pelvic chamber 14, an upper torso chamber 16, and a head chamber 18. Each of the above-noted seams may be formed by any appropriate method, such as by welding, melding, fusing, sewing or bonding. The provision of separately-inflatable chambers allows the support to specific areas of the human body to be fine-tuned (e.g., by adjusting the air volume and/or pressure within a chamber) to enhance patient comfort. It should be appreciated that the positioning and number of the chambers can be modified from that disclosed in the illustrated embodiment to achieve various support configurations. For example, a lumbar chamber may be provided by including an additional lateral seam in an appropriate location.

In the illustrated embodiment, longitudinally oriented seams 30a–f are formed in the pad 11 to provide additional structural stability and support to the pad, and to provide further comfort to the reclined patient. As illustrated in FIGS. 1–2, the chambers include longitudinal seams 30 which maintain the top surface of the pad in a relatively flat plane. For use as a catheter lab pad, the seams in the upper torso chamber 16 should be chosen to not interfere with imaging, particularly in the typical imaging angles. For example, it would be advantageous to avoid placing a seam down the middle of the upper torso chamber of the pad since it may interfere with imaging at the 0° position (described below). As such, there are only two seams 30e, 30f in the upper torso chamber 16 of the illustrated embodiment, thereby dividing the chamber into three relatively equal width segments, thereby leaving a large central zone for imaging at the 0° position.

The leg chamber 12 also includes two parallel longitudinal seams 30a, 30b, and the pelvic chamber 14 similarly includes two parallel longitudinal seams 30c, 30d. The longitudinal seams 30a–f are oriented substantially perpendicular to the lateral seams 28a–c and substantially parallel to the perimeter seam 26 running along the sides of the pad.

The longitudinal seams 30a–f are specifically designed to not divide the chambers into separate, sealed segments, thereby allowing all of the segments within a chamber to be inflated by a common inflation valve 24. It should be appreciated that the number and positioning of the longitudinal seams can be varied to enhance patient comfort. As with the perimeter and lateral seams 26, 28a–c, the longitudinal seams 30a–f can be formed by any appropriate method, such as welding, melding, fusing, sewing or bonding.

The perimeter, lateral and longitudinal seams 26, 28a–c, 30a–f are preferably of a sufficient width and strength to contain a volume of air for an extended period of time within the pad 11 (and therefore within chambers 12, 14, 16, 18) and to provide for a structurally stable pad 11. In the illustrated embodiment, the perimeter seam 26 measures approximately one-half (0.5) inch in width and each of the lateral seams 28a–c measures approximately one-quarter (0.25) inch in width. The longitudinal seams 30a–f each measure approximately one-eighth (0.125) inch in width. It should be appreciated that other seam widths could be utilized in practicing the present invention.

The dimensions of the pad and chambers are specifically designed to comfortably support a reclined patient. In the illustrated embodiment, the leg chamber 12 has a length which is about 20–50% of the overall length of the pad, the pelvic chamber 14 is about 5–30% of the length of the pad, the upper torso chamber 16 is about 20–50% of the length of the pad, and the head chamber 18 is about 5–30% of the length of the pad. Specifically, the inflated pad 11 measures about five (5) inches in height, about seventeen (17) inches in width, and about one-hundred and ten (110) inches in length. The leg chamber 12 of the illustrated embodiment is about forty-six (46) inches long, the pelvic chamber 14 is about sixteen (16) inches long, the upper torso chamber 16 is about thirty-two (32) inches long, and the head chamber is about sixteen (16) inches long. As shown in FIGS. 1–2, the head chamber is narrower than the other chambers and has a width of about eleven (11) inches.

In order to adequately support a patient's body, the pad 11 should be constructed from a strong, lightweight material. For example, the material may include nylon, aramid or other appropriate woven material. For use in x-ray imaging applications, the material should also be radiolucent. That is, the material should allow sufficient transmission of x-ray radiation to allow for effective internal imaging without the need for compensation by the imaging apparatus. Compensation by the imaging apparatus will automatically occur when the receiving unit of the apparatus receives less than a certain level of x-ray radiation, due to absorption and/or scattering of x-ray radiation being transmitted by the transmitting unit. As used herein, radiolucent means that at least 97% of the radiation contacting the pad is transmitted therethrough.

In the illustrated embodiment, the material comprises woven nylon fabric of about 70 denier. To reduce air loss through the fabric, the fabric is coated with an air impenetrable, waterproof coating 44, as illustrated in FIG. 3. Such coating may include urethane, vinyl or other appropriate polymer. In the illustrated embodiment, the coating 44 comprises a 0.005 inch layer of urethane on both sides of each sheet of material 13, 15.

Since no additional compensation is required to image through the pad 11, it can be appreciated that the patient and medical personnel will be exposed to decreased amounts of radiation during x-ray imaging. That is, lower X-ray transmission levels can be utilized compared to pads which require compensation. In addition, the lower amount of scatter which is believed to occur with the present invention reduces the radiation which may contact medical personnel.

Figure 4A:
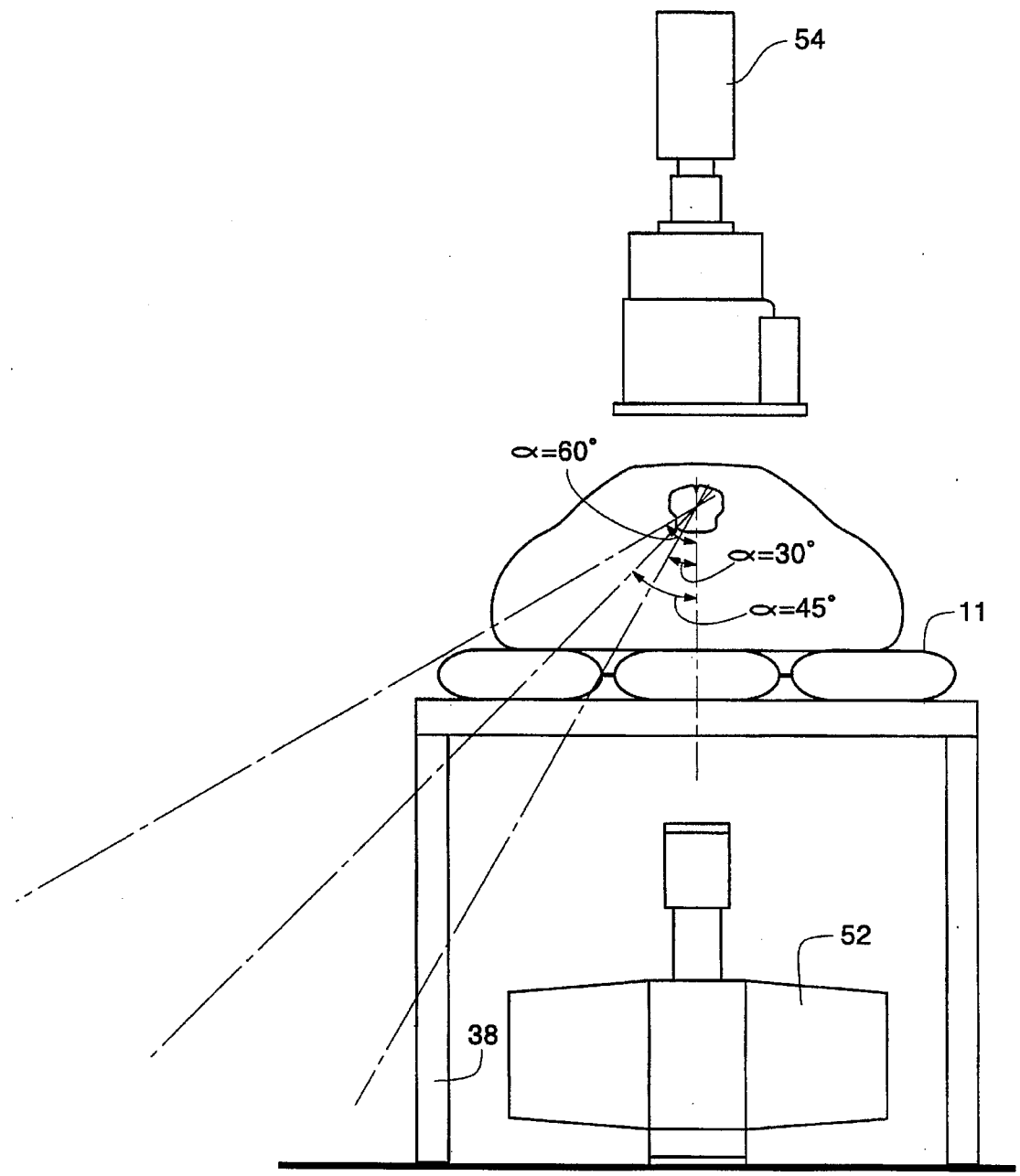
FIG. 4a is an end view of the inflated table pad with a reclined patient thereon and an imaging apparatus showing typical imaging camera angles relative to the heart.
Figure 4B:
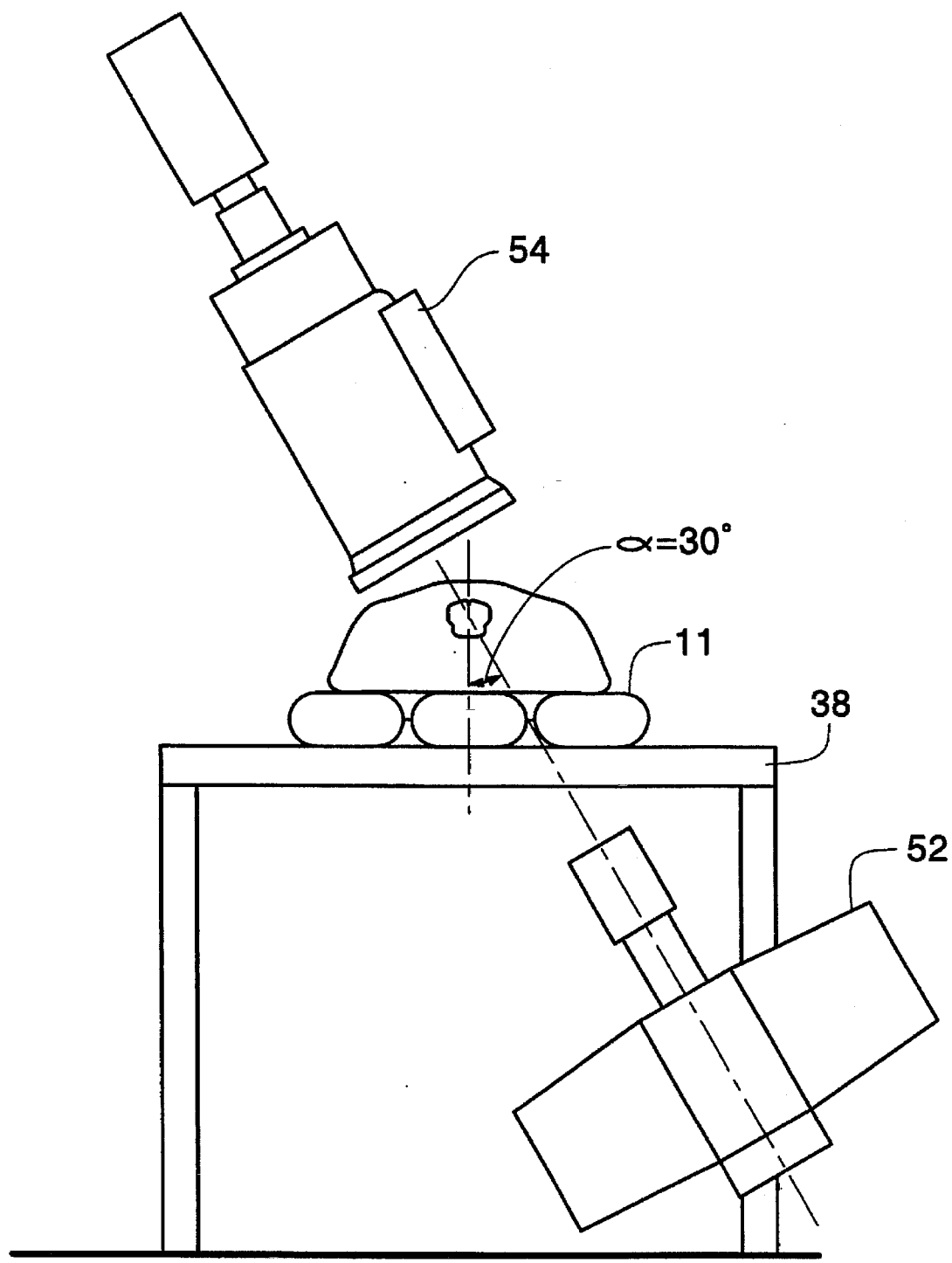
FIG. 4b is the end view of FIG. 4a with the imaging apparatus position at an angle relative to the table.

Unlike seams in many conventional pads, the lateral and longitudinal seams 28a–c, 30a–f of the pad 11 do not create substantial image artifacts during x-ray imaging due to the composition, size and location of such seams. Specifically, since the pad 11, and therefore the seams 28a–c, 30a–f, are made from a radiolucent material of a low denier, substantially no image artifacts are created by the seams 28a–c, 30a–f during x-ray imaging. In addition, proper location of the seams avoids a seam falling in the middle of an x-ray path. For example, in x-ray imaging of the coronary arteries, it is beneficial to take x-ray views from at least four different angular orientations relative to the heart. As illustrated in FIG. 4a, for purposes of coronary studies of the heart, the x-ray transmitter 52 and receiver 54 may be rotated about a longitudinally oriented axis, generally coinciding with a longitudinal axis of the patient through the heart (i.e., a cranial-caudal axis of the patient). To obtain images for use in such coronary studies, the x-ray transmitter 52 is typically angled at 0°, 30°, 45° and/or 60° relative to the heart (in either direction), herein denoted as the angle alpha ($\alpha$). By properly designing the structure of the pad, the longitudinal seams can be located to not interfere with the center of the typically-used x-ray angles, as illustrated in FIG. 4b. In a preferred embodiment, the longitudinal seams 30e, 30f are positioned approximately six and one-half (6.5) inches from each other, and are equally spaced from a center line of the pad. Due to the orientation, size and location of the longitudinal seams 30e, 30f in the upper torso chamber 16 of the illustrated pad 11 in relation to the position and angular orientation of the imaging device, the present apparatus 10 avoids imaging the heart where a longitudinal seams 30e, 30f covers the center of the x-ray beam. The result is a seam which is positioned at about 28° relative to the heart, thereby avoiding the above-noted angles (calculation based upon the distance from patient's heart to the seam approximately equal to about 6.0 inches). Thus, it can be appreciated that the present apparatus 10 is particularly useful in conducting typical coronary studies of a heart.

Figure 5:
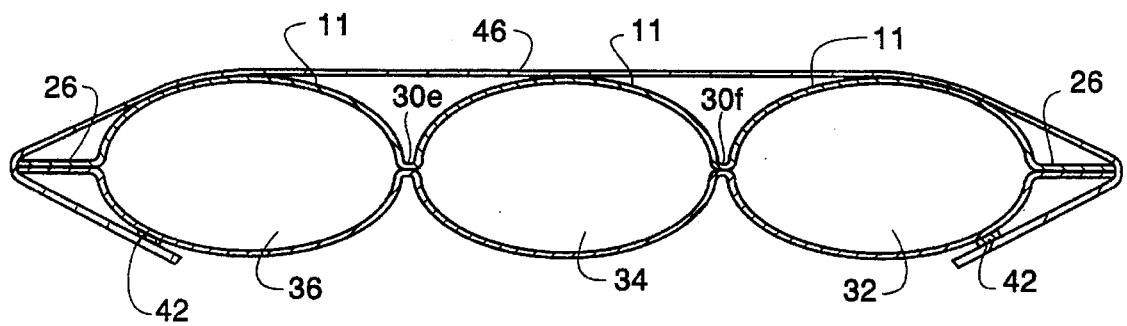
FIG. 5 is an enlarged section view of the inflated table pad through the perimeter and longitudinal seams, taken along line 5—5 of FIG. 2, with a cover secured to the inflated pad.

Referring to FIGS. 3, 4a, and 5, the illustrated pad also avoids creating image artifacts caused by the material of the pad 11 immediately adjacent the longitudinal seams 30a–f. Specifically, with regard to internal imaging of an area of the upper torso region of the reclined patient, when the upper torso chamber 16 is inflated to about atmospheric (e.g., with no patient positioned thereon) or a slight positive pressure (e.g., less than about 2 psi with a patient positioned thereon), the angle theta ($\Theta$) between the longitudinal seams 30e, 30f and the adjacent material of the pad 11 is substantially non-perpendicular. More specifically, when inflated with an air volume at about atmospheric pressure or at a slight positive pressure when the patient reclines on the pad 11, the angle theta ($\Theta$) is a non-perpendicular angle relative to the longitudinal seams 30e, 30f. In this regard, the segments 32, 34, 36 of upper torso chamber 16 of the pad 11 are not circular in cross-section when inflated to atmospheric or a positive pressure. Rather, when inflated with an air volume at about atmospheric pressure prior to patient placement on the pad 11, or to a slight positive pressure when a patient is positioned on the pad 11, the segments 32, 34, 36 have a substantially oblong cross-section, as illustrated in FIGS. 4a, 4b and 5.

It is believed that such non-perpendicular orientation of the material adjacent the seams further reduces image artifacts associated with the seams, at least in relation to imaging at the 0° position, since image artifacts can be created where the material of the pad 11 adjacent to the longitudinal seams 30e, 30f is parallel to the beam path of the x-ray. This aspect of the present invention, combined with the proper location of the longitudinal seams 30e–30f outside areas of interest at typical imaging angles as described above, provides for an apparatus 10 which does not require additional compensation to image through the seams 30e, 30f, thus providing a safer, more effective pad 11 for x-ray imaging.

To quantify the radiolucency of the above-described pad, tests were performed to compare the pad of the present invention to other currently-used pads. As a baseline, the intensity of an x-ray beam passing through the table without a pad was measured. At maximum system output of 110 KV, the intensity of the beam passing through the table equaled approximately 8.5 Roentgen/minute (R/min). When a standard currently-used pad (i.e., a urethane foam pad produced by Phillips Medical Systems) was placed onto the table, the intensity of the beam passing through the table and pad was 7.35 R/min, thereby resulting in a 13.5% reduction in beam intensity as a result scatter and/or absorption by the pad. Utilizing an egg crate foam pads having a 2.0 lb/ft.$^3$ density and a thickness of 3.0 inches, the beam intensity was 8.06 R/min, resulting in scatter and/or absorption of 5.2% of the beam. In contrast, using the illustrated pad on the table resulted in a beam intensity of 8.32 R/min which is a 2.1% decrease in beam intensity caused by scattering and/or absorption. Thus, it can be appreciated that the present apparatus avoids creation of significant image artifacts and scatters/absorbs less harmful radiation, thereby requiring less radiation and providing a safer work environment to medical personnel.

In order to ensure proper inflation of the pad 11 such that the segments 32, 34, 36 of upper torso chamber 16 are elliptical in cross-section and the material adjacent to the longitudinal seams 30a–f are not parallel to the beam path of the imaging camera, the inflation valves 24 and/or the inflation device (not shown) are capable of controlling the rate and/or the volume of air entering or exiting the pad 11. Preferably, where the pad 11 includes a number of chambers, each chamber 12, 14, 16, 18 is separately inflatable and/or deflatable. In this regard, in one embodiment, each chamber 12, 14, 16, 18 includes an inflation valve 24 such that each chamber 12, 14, 16, 18 may be separately inflated and/or deflated. The inflation valves 24 may also be capable of controlling the rate of inflation of air into the chambers 12, 14, 16, 18 and/or the rate of deflation of air out of the chambers 12, 14, 16, 18.

Figure 6:
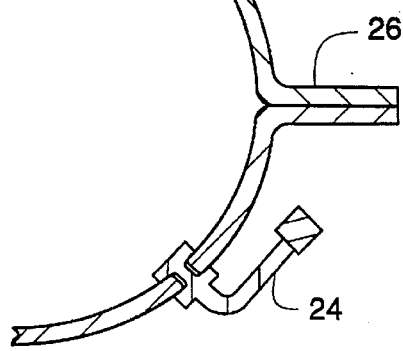
FIG. 6 is an enlarged section view of the inflated table pad through the perimeter seam and the inflation valve taken along line 6—6 in FIG. 2.

The inflation valves 24 should be readily accessible for efficient inflation and/or deflation of the pad 11 or chambers 12, 14, 16, 18 thereof. In this regard, as shown in FIG. 6, the inflation valves 24 may be positioned in close proximity to the perimeter seam 26, preferably on the bottom sheet 15 of each of the chambers 12, 14, 16, 18. Positioning the inflation valves 24 on the bottom sheet 15 of the pad 11 in close proximity to the seam provides for readily accessible inflation valves 24, especially where the apparatus 10 includes a cover 46 on the top side 13 of the pad 11. In addition, positioning on the bottom sheet 15 avoids contact of the valves 24 with the patient. In a preferred embodiment, the inflation valves 24 are positioned on the bottom sheet 15 of the pad 11 such that when the chambers 12, 14, 16, 18 are inflated to atmospheric or a slight positive pressure, the inflation valves 24 are substantially located on the side of the pad 11. Such accessibility of the inflation valves 24 when the pad 11 is inflated to atmospheric or a slight positive pressure facilitates efficient inflation and deflation of the pad 11 or the chambers 12, 14, 16, 18 thereof. Respiratory therapy air lines typically located in medical facilities, such as catheter laboratories, may be used to inflate the chambers 12, 14, 16, 18 of the pad 11. The inflation valve 24 preferably includes a flange and an insertion valve, such as a shank type insertion valve. For example, a Halkey Roberts 167-AC flange and a 260-AC insertion valve may be used.

Figure 7:
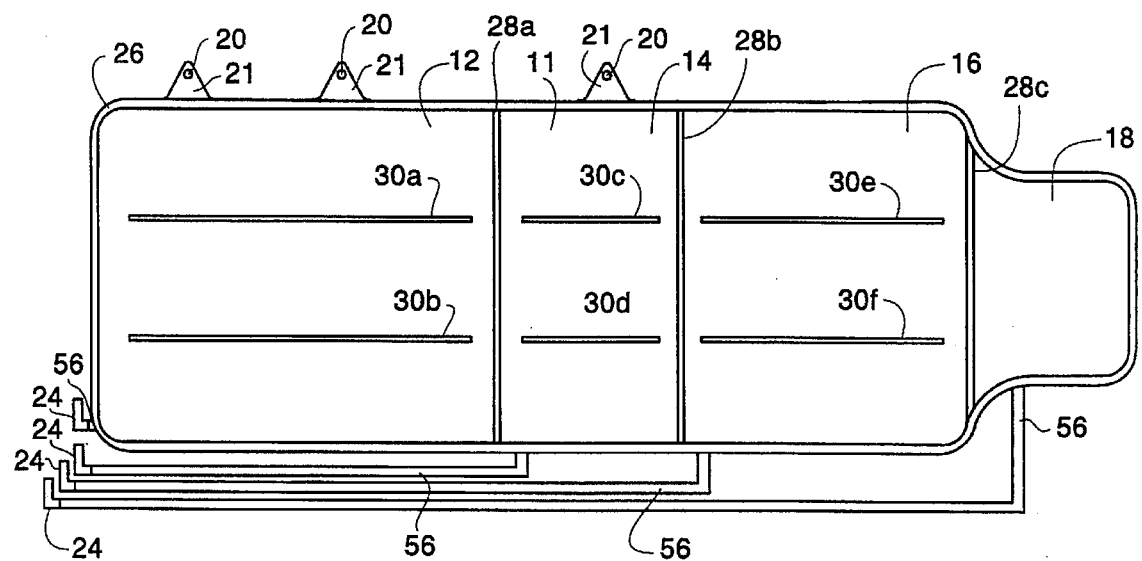
FIG. 7 is a top view showing an alternative embodiment of the table pad having inflation channels along a side of the pad.

In an alternative embodiment, the inflation valves 24 for each chamber 12, 14, 16, 18 may be positioned at an end of the pad 11, as shown in FIG. 7. In such an embodiment, each chamber 12, 14, 16, 18 may be provided with an inflation channel 56. Such inflation channels may, for example, be formed using tubing.

Figure 8:
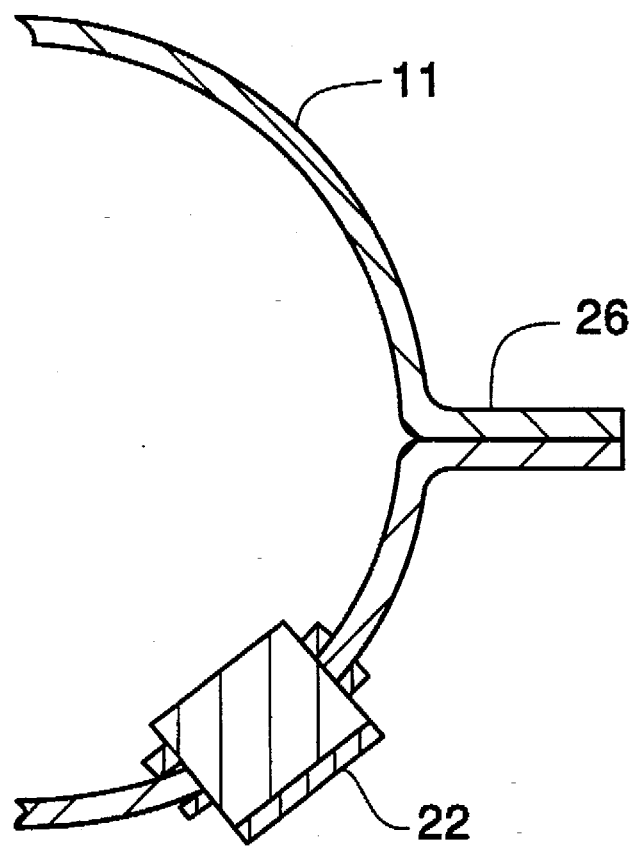
FIG. 8 is an enlarged section view of the inflated table pad through the perimeter seam and the relief valve, taken along line 8—8 in FIG. 2.

Referring to FIGS. 2 and 8, the pad 11 also includes a plurality of relief valves 22. Generally, the relief valves 22 provide a method for quickly removing air from the pad 11. In a preferred embodiment, the upper torso chamber 16 includes at least one relief valve 22 which releases air within the upper torso chamber 16 when the air within the upper torso chamber 16 is greater than or equal to approximately 2 pounds per square inch (psi). Such a relief valve 22 is especially beneficial to provide for a quick release of air from the upper torso chamber 16 when cardiopulmonary resuscitation (CPR) of the reclined patient on the pad 11 is necessary. That is, if CPR is required, the initial thrust onto the patient's chest will cause much of the air within the torso chamber 16 to be expelled through the respective relief valve 22, thereby positioning the patient in solid contact with the table to provide a solid support for performance of CPR. The relief valves 22 are Halkey Roberts 780SPFU-20 with a crack pressure of 2 psi. Preferably, to facilitate the release of air from the upper torso chamber 16 during CPR procedures, the relief valve 22 may be located on the bottom sheet 15 of the pad 11 in close proximity to the perimeter seam 26 and/or a lateral seam 28b, 28c. The relief valves 22 are positioned to be at an acute angle relative to the pad 11, preferably between about 10° and about 80°, and more preferably between about 30° and about 60°. In the illustrated embodiment, the relief valves 22 are at an angle of about 45°.

Figure 9:
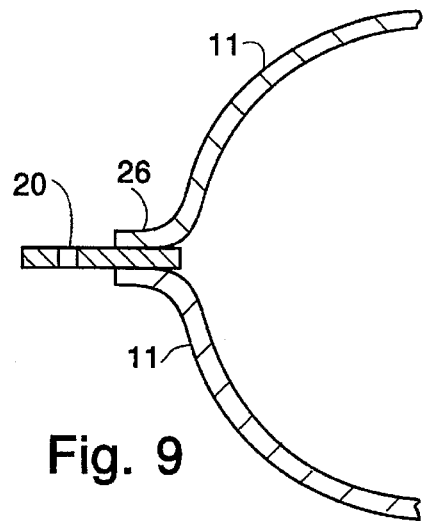
FIG. 9 is an enlarged section view of the inflated table pad through the perimeter seam and the grommet, taken along line 9—9 in FIG. 2.

Referring to FIGS. 1, 2, and 9, the apparatus 10 also includes a plurality of grommets 20. The grommets 20 allow the pad to be secured to the table 38, thereby providing further stability to the pad 11. In the illustrated embodiment, a plurality of grommets 20 are operatively associated with the pad 11 at various locations about the perimeter of the pad 11. To facilitate manufacture of the apparatus 10 and to provide for a secure interface between the grommet 20 and the pad 11, the grommets 20 may be located within the perimeter seam 26. In particular, at least one grommet 20 may be positioned along each of the longitudinal edges of the pad 11 within the perimeter seam 26. The grommets 20 may be composed of non-metallic material to avoid creation of image artifacts during internal imaging and to decrease radiation dispersal during x-ray imaging, which can be harmful to medical personnel. Preferably the grommets 20 are composed of the material of the pad 11 and attached or secured to the pad 11 along each of the longitudinal edges of the pad 11 within the perimeter seam 26, by welding, melding, fusing, sewing or bonding. Alternatively, the grommet 20 may be integrally associated with the top or bottom sheet 13, 15 of the pad 11. It can be appreciated that the grommets 20 may be rectangular, square, triangular, elliptical or other suitably shaped cross-section.

As shown in FIGS. 1, 3 and 5, the apparatus 10 may also include a disposable cover 46. Generally, the cover 46 serves two functions. First, the cover 46 preserves the pad 11 for reuse. Second, the cover 46 prevents drainage of fluids into the lateral and/or longitudinal seams 28a–c, 30a–f. The cover 46 accomplishes both of these tasks by covering at least the top sheet 13 of the pad 11 during internal imaging procedures. The cover 46 protects the pad 11 from rips, tears, or other damage, and prevents fluid build-up in the lateral and longitudinal seams 28a–c, 30a–f which can create image artifacts during x-ray imaging.

In order to sufficiently cover the top side 13 of the pad 11 and to provide for efficient placement on and removal from the pad 11, the cover 46 and/or the pad 11 may include a plurality of attachment devices 42, such as tape, velcro, snaps or other fasteners to detachably secure the cover 46 to the pad 11. In the illustrated embodiment of FIG. 5, double sided tape is used. Preferably, the cover 46 attaches to the pad 11 at various locations on the bottom sheet 15 of the pad, generally in close proximity to the perimeter seam 26, to provide access to the inflation valves 24 and facilitate inflation or release of air from the pad 11 or one or more of the chambers 12, 14, 16, 18 thereof. Alternatively, the cover 46 may be "fitted" such that the cover 46 snugly envelops at least the top sheet 13 of the pad 11. For example, the perimeter of the cover may be provided with an elastic band to allow securement of the cover to the pad in a manner similar to that of a fitted bed sheet to a mattress. For purposes of internal imaging, the cover 46 may be composed of a radiolucent material, such as polyethylene or other appropriate extruded polymer film. In the illustrated embodiment, the cover comprises polyethylene.

Figure 10:
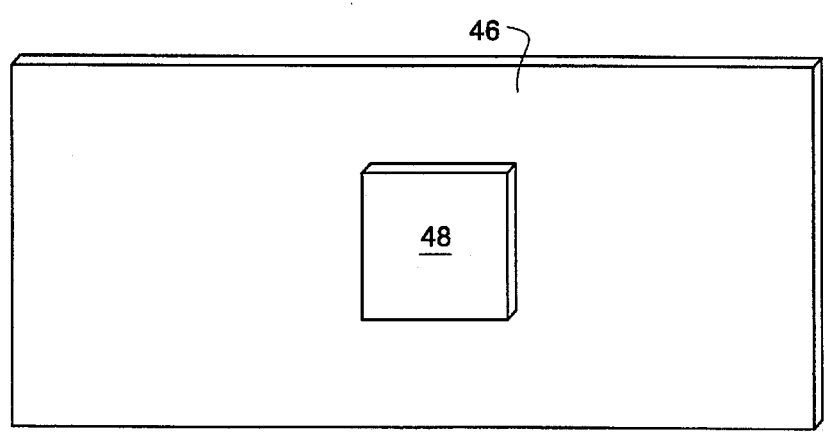
FIG. 10 is a perspective view showing an alternative embodiment of the cover.

In an alternative embodiment illustrated in FIG. 10, the cover 46 may also include an absorbent layer 48. The absorbent layer 48 may be secured to the cover 46 in the area underlying a patient's body region, such as the lumbar, pelvic and/or leg region, around which fluids are likely to drain. To avoid creating image artifacts, the absorbent layer 48 is preferably positioned on and attached to the cover 46 such that the x-ray imaging beam does not image through the absorbent layer 48 during internal imaging of a reclined patient on the pad 11. In the illustrated embodiment, the absorbent layer 48 comprises non-woven polypropylene composite, such as that sold as Kimberly-Clark Coform by Kimberly-Clark, and is detachably secured to the cover 46 using adhesive.

In another alternative embodiment of the present invention (not shown), the cover 46 may be shaped like a bag and may be fitted over the pad 11 such that the open end of the bag provides access to the inflation valves 24 located at one end of the pad 11 (e.g., the table pad embodiment shown in FIG. 7). The disposable bag may be provided with a peel-away absorbent layer 48, as described above. Upon removal and disposal of the absorbent layer 48, the disposable bag may be turned inside out and utilized as a trash disposal bag. Furthermore, the bag may be composed of radiolucent material to avoid creating image artifacts. In this regard, the bag may also be seamless, especially in the region of the beam path from the imaging apparatus.

The present invention also includes a method for comfortably supporting a patient on a table 38. The present method includes the steps of placing a pad 11 on a table 38, positioning a patient on the pad 11, and inflating the pad 11. The uninflated pad 11 should first be placed or positioned upon a table 38 such that the bottom sheet 15 of the pad 11 contacts the table 38 and the top side 13 of the pad 11 can contact the patient. The inflation valves 24 and relief valves 22 should also contact the table 38 when the pad is uninflated. Once the uninflated pad 11 is positioned on the table 38, a cover 46 may be placed over the top side 13 of the pad 11 and fastened to the bottom sheet 15 of the pad 11. The cover 46 should be spread over at least one of the chambers 12, 14, 16, 18 of the pad 11 and preferably, over at least the entire top side 13 of the pad 11 such that the edges of the cover 46 slightly overlap the perimeter seam 26 of the pad 11. However, in a preferred embodiment, the cover 46 should not substantially extend beyond the perimeter seam 26 because the cover 46 should not inhibit the functions of the relief and inflation valves 22, 24.

Once positioned on the top sheet 13 of the pad 11, the cover 46 may be fastened to the pad 11 at a plurality of locations, preferably on the bottom sheet 15 of the pad 11. In a preferred embodiment of the present invention, the cover 46 includes a number of locations where strips of adhesive 42, preferably double-sided tape, may be fastened or adhered to the bottom sheet 15 of the pad 11 at various locations. Alternatively, where the cover 46 is a bag, the pad 11 may be slid into the bag such that the bag substantially envelops the pad 11 and the inflation valves 24 are substantially accessible at the open end of the bag.

Once the cover 46 has been positioned and secured over the top side 13 of the pad 11, the patient may be placed on the pad 11, typically in a reclined or prone position. After the patient has been positioned on the pad 11, the pad 11 may be inflated. Inflating the pad 11 after the patient has been positioned on the pad 11 enables the patient to provide feedback to personnel inflating the pad 11 as the pad 11 is inflated, thereby allowing the patient some control over the procedure and allowing the patient to choose the most comfortable inflation pressure in each chamber of the pad. Subject to the discretion of the patient, the chambers 12, 14, 16, 18 may be inflated to an atmospheric or slight positive pressure which provides a substantial degree of comfort to the patient.

Preferably, the chambers 12, 14, 16, 18 of the pad 11 are inflated sequentially while the patient is reclined on the pad 11. In this regard, for purposes of providing comfort to the patient, the head chamber 18 may be inflated first. Once the head chamber 18 is inflated to an atmospheric or a positive pressure of less than two (2) psi, the upper torso chamber 16 may be inflated to an atmospheric or a positive pressure of less than two (2) psi, followed by inflation of the pelvic chamber 16 and the leg chamber 12 to an atmospheric or a positive pressure of less than two (2) psi. In one embodiment, the head chamber is inflated before the patient is positioned on the pad, thereby providing cushioned support to the patient's head at the initiation of the procedure.

Preferably, to obtain elliptical shaped cross-sections 32, 34, 36, the upper torso chamber 16 is inflated to approximately atmospheric pressure such that the material adjacent to the longitudinal seams 30e, 30f is not parallel to the beam path of the imaging device (e.g., when imaging at the 0° position). The chambers 12, 14, 16, 18 may be inflated with air by any suitable inflation device, such as respiratory therapy air lines in catheter laboratories. In addition, where the inflation valve 24 is a shank type insertion valve, the rate of inflation may be controlled by rotating the inflation valve 24, or alternatively, the rate of inflation may be controlled by the inflation device.

The method of the present invention may also include the step of adjusting the pressure in each section for patient comfort. With regard to the chamber through which imaging will occur, such as the upper torso chamber 16, the pressure may be adjusted to ensure that the cross-sectional shape of the portions 32, 34, 36 are oblong. The pressure in each chamber 12, 14, 16, 18 may be adjusted by opening the inflation valves 24 for a period of time to release an amount of air within the selected chamber to be adjusted. In any event, the relief valves 22 are designed to release air within the chambers 12, 14, 16, 18 when the pressure within the chambers 12, 14, 16, 18 is greater than or equal to two (2) psi.

Alternatively, the pad 11 may be inflated prior to positioning the patient on the pad 11. In such instances, the pad 11, or chambers 12, 14, 16, 18 thereof, may be inflated to about atmospheric pressure. The patient may thereafter be placed on the pad 11. For purposes of providing comfort to the patient, the pressure within the chambers 12, 14, 16, 18 of the pad 11 may thereafter be adjusted as described above until the patient is comfortable.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. In a process for performing catheter lab imaging on the heart of a patient utilizing a catheter lab imaging apparatus comprising a catheter lab table, an x-ray transmitter, and an x-ray receiver, the improvement comprising the steps of:

positioning a pneumatic pad on the table, the pad including a radiolucent portion positioned in an imaging region of the table, and the pad further including seams;

inserting gas into the pad to at least partially inflate the pad;

positioning the patient in a reclined position on the pad such that the patient's heart is aligned with the radiolucent portion of the pad;

imaging the heart of the patient while performing a catheter lab procedure, wherein the imaging apparatus images along predetermined imaging axes, wherein said positioning the pad step comprises positioning the seams to avoid interference with the imaging axes;

removing the patient from the pad; and removing the gas from the pad to deflate the pad.

2. A method as claimed in claim 1, wherein the predetermined imaging axes extend through the patient's heart at angles of 0°, 30°, 45°, and 60° relative to an axis extending perpendicular to the table.

3. A method as claimed in claim 1, wherein said inserting gas step occurs before said patient positioning step, and wherein said inserting gas step comprises filling the pad with gas to a pressure of less than about 1 psi.

4. A method as claimed in claim 3, wherein said pressure is about atmospheric pressure.

5. A method as claimed in claim 1, wherein said inserting gas step occurs before said patient positioning step, and wherein said inserting gas step comprises filling the pad with gas to less than maximum volume of the pad.

6. A method as claimed in claim 1, wherein said patient positioning step occurs before said inserting gas step, and wherein said inserting gas step comprises filling the pad with gas to less than about 2 psi.

7. In a process for performing catheter lab imaging on the heart of a patient utilizing a catheter lab imaging apparatus comprising a catheter lab table, an x-ray transmitter, and an x-ray receiver, the improvement comprising the steps of:

positioning a pneumatic pad on the table, with a radiolucent portion of the pad positioned in an imaging region of the table;

inserting gas into the pad to at least partially inflate the pad;

positioning a waterproof cover on the pad;

positioning the patient in a reclined position on the pad such that the patient's heart is aligned with the radiolucent portion of the pad;

imaging the heart of the patient while performing a catheter lab procedure;

removing the patient from the pad; and removing the gas from the pad to deflate the pad.

8. A method as claimed in claim 7, further comprising, after said removing patient step, the step of removing the waterproof cover from the pad.

9. A method as claimed in claim 7, wherein the cover includes an absorbent material secured thereto, and wherein said method further comprises the step of positioning the absorbent material under the upper leg and hip region of the patient.

10. A method as claimed in claim 9, wherein the absorbent material is detachably secured to the cover, and wherein the method further comprises the step of detaching the absorbent material from the cover.

11. A method as claimed in claim 7, wherein said waterproof cover is bag-shaped to substantially cover a top surface, a bottom surface and at least one end of the pad, and wherein said method further comprises, after said removing the waterproof cover step, the steps of:

turning the waterproof cover inside out; and using the waterproof cover to contain waste produced during said imaging step.

12. In a process for performing catheter lab imaging on the heart of a patient utilizing a catheter lab imaging apparatus comprising a catheter lab table, an x-ray transmitter, and an x-ray receiver, the improvement comprising the steps of:

positioning a pneumatic pad on the table, with a radiolucent portion of the pad positioned in an imaging region of the table, wherein the pad comprises at least head and torso sections;

inserting gas into the pad to at least partially inflate the pad;

positioning the patient in a reclined position on the pad such that the patient's heart is aligned with the radiolucent portion of the pad, wherein the patient is placed on the pad before the torso section is inflated and after the head section is inflated;

imaging the heart of the patient while performing a catheter lab procedure;

removing the patient from the pad; and removing the gas from the pad to deflate the pad.

* * * * *